United States Patent [19]

Augustine et al.

[11] Patent Number: 5,217,695
[45] Date of Patent: Jun. 8, 1993

[54] VOLUMETRIC CHEMICAL REACTION SYSTEM

[75] Inventors: Robert L. Augustine, Livingston; Setrak K. Tanielyan, South Orange, both of N.J.

[73] Assignees: Philip Morris Incorporated, New York, N.Y.; Philip Morris Products Inc., Richmond, Va.

[21] Appl. No.: 757,567

[22] Filed: Sep. 11, 1991

[51] Int. Cl.$^5$ .............................................. G05D 7/00
[52] U.S. Cl. ................................ 422/111; 422/114; 422/115; 422/108; 422/129
[58] Field of Search ............... 422/110, 111, 112, 113, 422/114, 115, 26, 295, 129, 131, 108; 364/500

[56] References Cited

U.S. PATENT DOCUMENTS

| | | | |
|---|---|---|---|
| 2,638,919 | 5/1953 | Clarridge | 137/84 |
| 4,164,538 | 8/1979 | Young et al. | 422/26 |
| 4,261,950 | 4/1981 | Bainbridge et al. | 422/26 |
| 4,294,804 | 10/1981 | Baran | 422/112 |
| 4,576,194 | 3/1986 | Lucas et al. | 137/84 |
| 4,679,583 | 7/1987 | Lucas et al. | 137/84 |
| 4,687,635 | 8/1987 | Kaehler et al. | 422/26 |
| 4,971,764 | 11/1990 | Albright | 422/110 |

Primary Examiner—Robert J. Warden
Assistant Examiner—T. A. Trembley
Attorney, Agent, or Firm—James E. Schardt

[57] ABSTRACT

This invention provides a multipurpose volumetric chemical reaction system which operates at constant pressure and volume, and has electronic automation means for calculating kinetic parameters and a concentration-time plot from the system data output.

The automated system is adapted to conduct and monitor either gas-consuming or gas-generating reactions. Gas input or gas venting is accomplished in timed constant volume pulses.

7 Claims, 2 Drawing Sheets

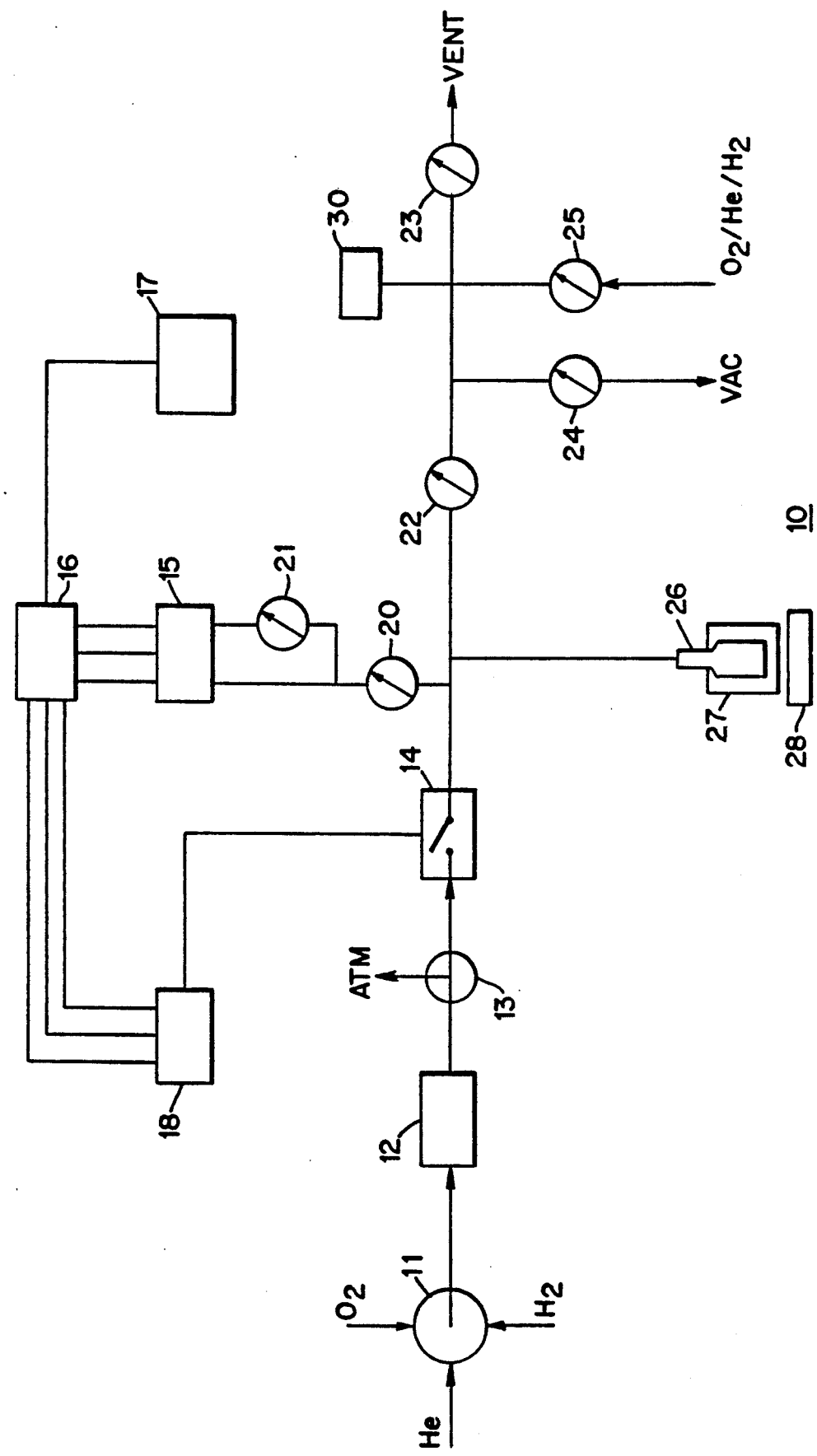

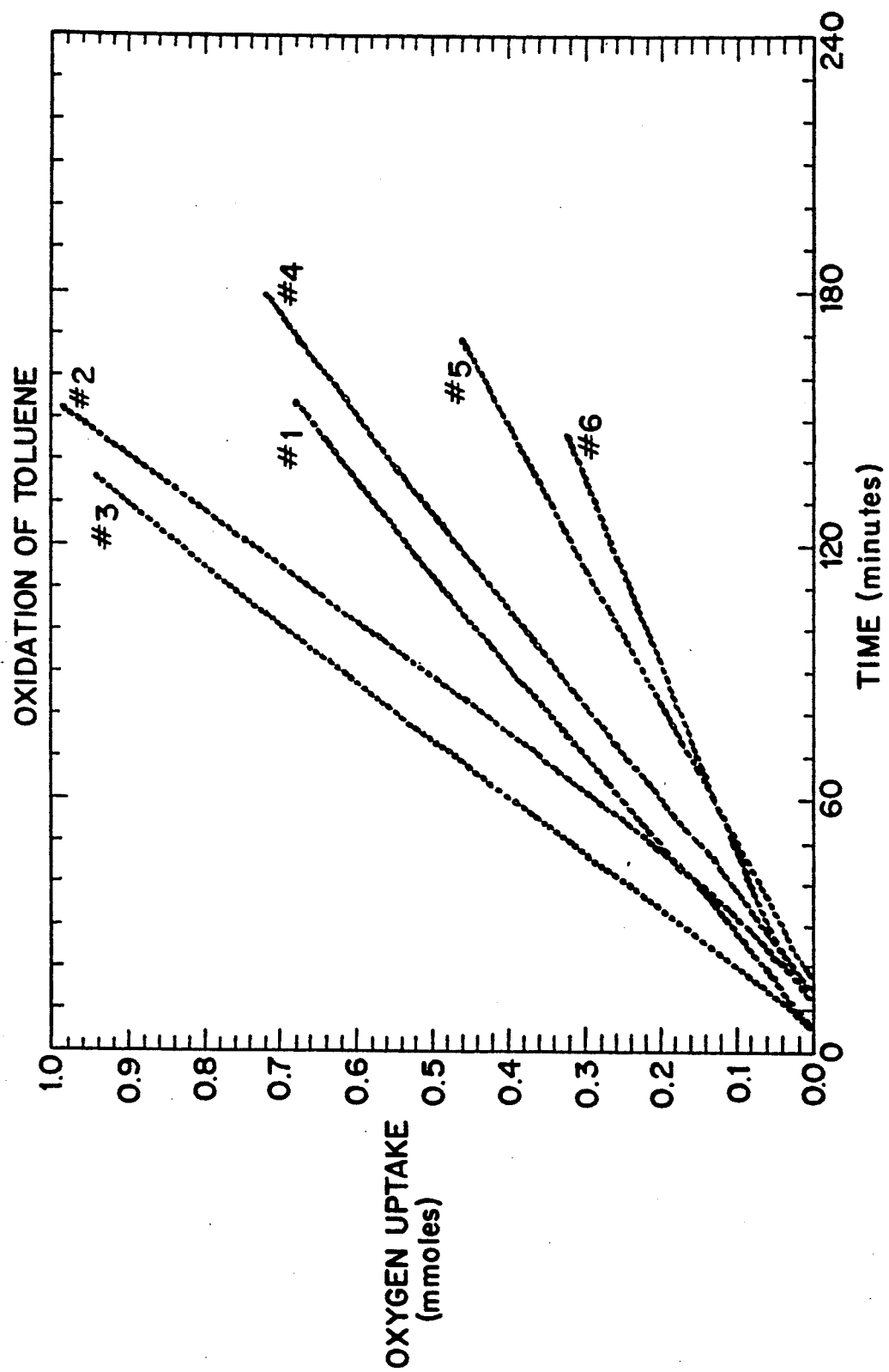

VOLUMETRIC CHEMICAL REACTION SYSTEM

BACKGROUND OF THE INVENTION

There are two categories of apparatus designs which are utilized to measure the extent of gas uptake or evolution during a chemical reaction. In one type the pressure of the gaseous reactant or gas evolved is kept constant by changing the volume the gas occupies within the reaction apparatus with the extent of gas consumption or evolution determined by the volume change required to maintain constant pressure. In the second type the volume of the system remains constant and the amount of gas consumed or evolved is determined by the corresponding pressure change. The first type of system is used almost exclusively for reactions conducted at or near atmospheric pressure, while the second type generally is operated at elevated pressures.

Constant pressure systems provide a more meaningful interpretation of reaction results since in such systems the amount of gas present per unit volume remains constant. In constant volume systems the amount of gas available for further reaction is constantly decreasing thus making the evaluation of reaction rate data more complex.

Automation of the constant volume systems is not a factor in equipment design since the only change in the system is the internal pressure, a change which occurs as the gas is either consumed or evolved. Automated recording of this pressure change can be accomplished with a pressure sensing means such as a pressure transducer or similar device within the system which measures the output of the pressure sensing means with time.

Automation of the constant pressure apparatus is more complex. In these systems the pressure is kept constant by using various methods to automatically change the volume of the system as the gas is consumed or evolved. This can be accomplished manually by raising or lowering a levelling bulb filled with a liquid and attached to the bottom of a gas burette by a flexible tube. Automation of such systems has been achieved by the use of a motor driven device to raise or lower the bulb with the motor being regulated by impulses from a pressure sensing device. When the device detects a small pressure change, the motor is actuated and the gas volume is adjusted to regain the original operating pressure. The use of a motor driven threaded metal rod to displace an appropriate volume of gas is described in Chem. and Ind., 1125 (1971).

Another technique is to use a motor driven gas syringe to change the volume of the system as described in publications such as Rev. Sci. Instr., 37, 1734 (1966), and 39, 590 (1968); and Magy. Kem. Foly., 79, 212 (1973). Such an apparatus can be used at elevated pressures as well as atmospheric. The motors employed in these systems are reversible, frequently driven by servo mechanisms and usually attached to a multiturn variable resistor so the gas volume can be electronically recorded. In all of these systems the capacity is determined by the size of the burette or syringe, and it is necessary to change the size of the gas holding device to vary the scale of the reactor.

Other device designs are used to record and control the pressure within a gas reaction apparatus, such as those described in U.S. Pat. Nos. 2,638,919; 4,576,194; and 4,679,583. However, none of these devices have provisions for recording the volume changes associated with the pressure regulation.

All of the known automatic systems generally have both mechanical and electrical features which are difficult to design and build, and which are subject to the wear associated with mechanical systems.

There is continuing interest in the development of improved apparatus designs in which gas consumption or gas evolution during a chemical reaction is measured.

Accordingly, it is an object of this invention to provide a volumetric chemical reaction system which is adapted to conduct and monitor a gas-consuming or gas-evolving reaction.

It is a further object of this invention to provide a chemical reaction system which operates at constant pressure and volume, and has automated means for calculating kinetic parameters and a concentration-time plot from the system data output.

Other objects and advantages of the present invention shall become apparent from the accompanying description and Example, and drawings.

DESCRIPTION OF THE INVENTION

One or more objects of the present invention are accomplished by the provision of a volumetric chemical reaction system comprising:

(a) a reactor unit;
(b) a pulse valve means connected to the reactor unit for supplying a gas reactant to the reactor unit or venting evolved gas from the reactor unit in a pulsed quantity;
(c) a pressure sensing means for producing a signal which is proportional to differential pressure in the reactor unit;
(d) an analog-digital converter and computer means which is activated by the pressure sensing means signal; and
(e) an electronic timing circuit means which is activated by a computer signal and which controls the timing of a constant pulse duration of a constant gas volume flow through the pulse valve means.

In a more specifically defined embodiment this invention provides a volumetric reaction system comprising:

(a) a reactor unit;
(b) a solenoid pulse valve means connected to the reactor unit;
(c) an external valve means connected to the solenoid pulse valve means for supplying a gas reactant to the reactor unit or venting evolved gas from the reactor unit in a pulsed quantity through the solenoid pulse valve means;
(d) a pressure transducer means for sensing the reactor unit pressure;
(e) an analog-digital converter and computer means which is activated by the pressure transducer electronic output; and
(f) an electronic timing circuit means which is activated by a computer signal and which controls the timing of a constant pulse duration of a constant gas volume flow through the solenoid pulse valve means.

The invention volumetric chemical reaction system is adapted to conduct and monitor gas-consuming reactions such as hydrogenation, oxidation, carbonylation, or polymerization.

The invention reaction system also has utility for conducting and monitoring gas-evolving reactions such as peroxide decomposition, decarboxylation and decarbonylation.

The invention reaction system computer means is adapted to calculate kinetic parameters and provide a concentration-time plot from the reaction system data output.

The invention volumetric chemical reaction system can be operated with a fully automated control of constant volume and pressure.

Mechanical breakdown is essentially eliminated, since the pulse valve means is the only mechanical component in the system.

BRIEF DESCRIPTION OF THE DRAWINGS

Specific embodiments of the present invention are illustrated in the following Example and drawings.

FIG. 1 is a schematic representation of a present invention volumetric chemical reaction system which is adapted to conduct and monitor hydrogenation or oxidation reactions.

FIG. 2 is a graphic representation of the oxygen gas utilization rates for the oxidative acetoxylation of toluene over different palladium-tin catalysts as described in the Example and Table I.

Referring to FIG. 1, reaction system 10 is an integrated, fully automated combination of interconnected gas conduits, valves, reaction zone and computer means, which under operational conditions maintains a constant pressure and volume in the reaction zone.

In the operation of reaction system 10 in FIG. 1 with respect to the oxidative acetoxylation conditions described in the Example, a gas source supplies oxygen through valve 11 (4-way ball valve, Whitey SS-43YFS2), and pressure regulator 12 (Scott 41-23A-10, 0-10 psig, with 54-68C-15 0-15 psig gauge) maintains the incoming oxygen pressure slightly higher than the reaction zone pressure. Valve 13 (three-way valve, Whitey SS-41XS2) is utilized as a multipurpose means to switch between gas-consuming and gas-evolving reaction modes. During a gas-evolving operation, gas is vented to the atmosphere through valve 13.

Solenoid pulse valve 14 (Matheson 8241-0422) introduces a calculated constant volume of oxygen in a timed pulse of constant duration. In a gas-evolving operation, solenoid pulse valve 14 vents a constant volume of gas through valve 13 in a timed pulse of constant duration.

Pressure transducer 15 (Omega PX163-005BD-5V) senses differential pressure in the reaction zone, and transmits a signal through analog/digital converter 16 (Metrabyte DAS-8PGA with STA-08PGA terminal board) and actuates computer 17 (IBM compatible PC). Timing device 18 is a monostable microprocessor which is triggered by a signal from computer 17, and times the gas pulse function of solenoid pulse valve 14.

Valves 20-25 are 2-way ball valves (Whitey SS-41S2). Prior to the commencement of the initial preparative procedures, valve 20 is closed to isolate sensitive pressure transducer 15 from the reaction zone.

Reactor 26 is in combination with thermostating means 27 and magnetic stirring means 28. Reactor 26 is charged with a reaction medium a described in the Example. The reaction zone is evacuated and flushed, and pressured with oxygen gas, by means of valves 22-25 and pressure transducer 30 (Omega PX243-2.5BG-5V).

Valve 20 and valve 21 are opened to expose the reference and working functions of pressure transducer 15 to the reaction zone pressure. Valve 21 then is closed to retain the equilibrated reaction zone pressure as a reference for computer 17.

The oxidative acetoxylation reaction is initiated, and a sequence of signals from computer 17 actuates the input of pulsed oxygen gas volumes through solenoid pulse valve 14 in a sequence corresponding to the rate of oxygen gas consumption as graphically represented in FIG. 2.

EXAMPLE

This Example illustrates the preparation of palladium-tin catalysts, and the use of the catalysts for the oxidation of toluene in a present invention volumetric chemical reaction system.

A 250 ml three-necked flask equipped with a magnetic stirring bar, thermometer, bubbler and a septum was charged with 15 ml of $H_2O$ and 5 g of $SiO_2$ (Davidson grade 952, acid washed, calcined at 400° C. for 4 hours, 80-120 mesh, BET surface area of 322.5 $m^2/g$). To this suspension was added with stirring 16.8 ml of a $SnCl_2.2\ H_2O$ solution (1.28 g of $SnCl_2.2\ H_2O$ and 0.4 ml of 6M HCl in 100 ml of $H_2O$) at a rate of 10 ml/min., and the mixture was stirred for 30 minutes. To the resulting suspension was added 18.8 ml of sodium hydroxide (2.4 g of NaOH in 500 ml of water) at a rate of 10-15 ml/min. The aqueous medium of the slurry had a pH value of 4-4.2 and gave a negative test for $Sn^{2+}$ (characteristic reaction with $HAuCl_3$).

The reaction vessel was purged with He for 10 minutes at a flow rate of 20 ml/min., and immersed in a silicon oil bath heated at 55° C. When the temperature of the slurry reached 45°-50° C., 8.4 ml of a $Na_2PdCl_4$ solution (1.66 g of $Na_2PdCl_4$ dissolved in 100 ml of water) was added at a rate of 2-3 ml/min., and the mixture was stirred for 30 minutes. The slurry solids were separated by centrifugation and washed several times with a dilute acetic acid solution (pH, 4-4.2) until the absence of a detectable quantity of $Cl^-$ in the washing liquid ($AgNO_3$). The resulting catalyst product (1% wt of Pd) was dried in air at 95° C. for 12 hours. The catalyst then was loaded in a Pyrex glass tube (0.30/0.006 m/m) in two portions with a He flow of 20ml/min. and with a temperature program of 10 min. at 25° C., ramping at 20°/min. to 300° C., and holding at 300° C. for two hours.

Using the same procedures described above, catalysts were prepared having a range of different concentrations of $SnCl_2$ and $Na_2PdCl_4$ (with the same atomic ratio of Sn:Pd=2). The relative activities of samples #1-6 in Table I and FIG. 2 were determined by the oxidation of toluene in the invention reaction system illustrated in FIG. 1. The rate of oxygen consumption was measured as a criterion of catalyst activity. During each toluene oxidation run, the accumulation of benzylacetate(1) and benzylidene diacetate(2) was monitored using GC analysis, and in all the cases the ratio of (1):(2) was in the range of 3-3.2:1.

For each toluene oxidation run, 1 gram of a supported Pd-Sn catalyst, 0.392 gram of KOAc (0.4 mol/1), 1.4 ml of toluene (1.3 mol/1) and 8.6 ml of acetic acid were charged to reactor 26 in FIG. 1. The system was alternately evacuated and filled with oxygen three times. The pressure was adjusted to atmospheric, and the reaction flask was placed in thermostating bath 27 set at 70° C. After a two minute equilibration time, the oxygen uptake (about 0.25 cc pulse volume) was measured using the computerized monitoring system. After the rate of oxygen uptake decreased significantly as indicating a near complete reaction, an aliquot of reaction medium was withdrawn from reactor 26 and analyzed by gas chromatography. The product mixture was composed of benzylacetate and benzylidenediacetate in near quantitative yield.

TABLE I

| # | % Pd | Rate, mmol $O_2$/min. |
|---|------|------------------------|
| 1 | 0.75 | $4.80 \times 10^3$ |
| 2 | 1.00 | 7.83 |
| 3 | 1.25 | 7.60 |
| 4 | 1.50 | 4.47 |
| 5 | 1.90 | 3.02 |
| 6 | 2.60 | 2.51 |

What is claimed is:

1. A volumetric chemical reaction system comprising:
   (a) a reactor vessel;
   (b) a pulse valve means connected to the reactor vessel for supplying a gas reactant to the reactor vessel or for venting evolved gas from the reactor vessel in a pulsed quantity;
   (c) a pressure sensing means connected to the reactor vessel for producing a signal which is proportional to pressure change in the reactor vessel;
   (d) an integrated analog-digital converter and computer means which is connected to the pressure-sensing means and activated by the pressure sensing means signal to transmit a computer signal; and
   (e) an electronic timing circuit means which is connected to the computer means and is activated by the computer signal and controls the timing of constant volume gas pulses through the pulse valve means.

2. A volumetric chemical reaction system comprising:
   (a) a reactor vessel;
   (b) a solenoid pulse valve means connected to the reactor vessel;
   (c) an external valve means connected to the solenoid pulse valve means for supplying a gas reactant to the reactor vessel or venting for evolved gas from the reactor vessel in a pulsed quantity through the solenoid pulse valve means;
   (d) a pressure transducer means connected to the reactor vessel for sensing the reactor vessel pressure;
   (e) an integrated analog-digital converter and computer means which is connected to the pressure transducer means and activated by the pressure transducer electronic output to transmit a computer signal; and
   (f) an electronic timing circuit means which is connected to the computer signal and is activated by the computer signal and control the timing of constant volume gas pulses through the solenoid pulse valve means.

3. A chemical reaction system in accordance with claim 2 wherein the computer means is programmed to calculate kinetic parameters and provide a concentration-time plot from the chemical reaction system timing data of pulsed gas volume flow.

4. A chemical reaction system in accordance with claim 2 wherein a gas reactant source is connected to the external valve means at a higher pressure than the chemical reaction system.

5. A chemical reaction system in accordance with claim 2 wherein the electronic timing circuit means is an internal computer capability.

6. A chemical reaction system in accordance with claim 2 wherein the electronic timing circuit means is a monostable microprocessor which is activated by a computer signal.

7. A chemical reaction system in accordance with claim 2 which has a valve means for isolating the pressure transducer means during preparative procedures prior to initiation of a chemical reaction being conducted and monitored.

* * * * *